United States Patent [19]

Jiang

[11] Patent Number: 4,596,805

[45] Date of Patent: Jun. 24, 1986

[54] SUBSTITUTED DIOXOPYRIDOPYRIMIDINES

[75] Inventor: Jack B. Jiang, Wilmington, Del.

[73] Assignee: Ortho Pharmaceutical Corporation, Raritan, N.J.

[21] Appl. No.: 620,588

[22] Filed: Jun. 13, 1984

[51] Int. Cl.$^4$ ............... C07D 471/04; C07D 487/04; A61K 31/505
[52] U.S. Cl. .................................. 514/258; 544/279
[58] Field of Search .................. 424/251; 544/279; 514/258

[56] References Cited

U.S. PATENT DOCUMENTS

| | | | |
|---|---|---|---|
| 2,926,166 | 2/1960 | Hitchings | 544/279 |
| 4,304,914 | 12/1981 | Shroff et al. | 546/123 |
| 4,321,384 | 3/1984 | Sulkowski et al. | 546/123 |

FOREIGN PATENT DOCUMENTS

| | | | |
|---|---|---|---|
| 2334266 | 1/1974 | Fed. Rep. of Germany | 544/279 |
| 2738153 | 8/1977 | Fed. Rep. of Germany | 544/279 |

*Primary Examiner*—George F. Lesmes
*Assistant Examiner*—S. A. Gibson
*Attorney, Agent, or Firm*—Geoffrey G. Dellenbaugh

[57] ABSTRACT

Substituted dioxopyridopyrimidines are provided which are useful as calcium antagonists and anti-hypertensive agents.

8 Claims, No Drawings

SUBSTITUTED DIOXOPYRIDOPYRIMIDINES

FIELD OF THE INVENTION

The present invention relates to novel substituted dioxopyridopyrimidines which are useful as calcium antagonists and anti-hypertensive agents and may be used for treating coronary disease.

BACKGROUND OF THE INVENTION

A number of chemical compounds termed "calcium antagonists" or "calcium blockers" are known. Representative compounds of this type are disclosed, for example, in U.S. Pat. Nos. 4,304,914 and 4,321,384. These calcium blockers have been found useful in the treatment of hypertension, cardiac arrhythmia, angina pectoris, and a variety of other cardiac disfunctions.

Certain dioxopyridopyrimidines are disclosed in German published patent application No. 27,38,153; see especially Example 43. The subject compounds differ from those of this German patent application principally in the methyl substituent on the 7-position.

SUMMARY OF THE INVENTION

The compounds of the present invention are substituted dioxopyridopyrimidines having the formula:

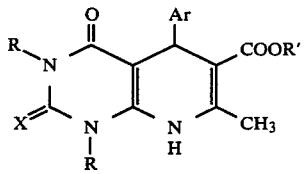

and the pharmaceutically-acceptable acid addition salts thereof, wherein;
R is hydrogen or loweralkyl;
Ar is aryl, furanyl, or cyclohexyl;
R' is loweralkyl, loweralkyl substituted by a halo or trifluoromethyl group, or (arylloweralkyl) (loweralkyl) aminoloweralkyl; and
X is O or S;
said aryl being phenyl or phenyl substituted with 1 or 2 substituents independently selected from the group consisting of halo, nitro, cyano, loweralkyl, loweralkyloxy, and trifluoromethyl.

As used herein, the term "halo" includes fluoro, chloro, bromo, and iodo. The term "loweralkyl" includes straight- and branched-chain saturated hydrocarbons having from 1 to 6 carbon atoms, such as methyl, ethyl, n-propyl, isopropyl, n-pentyl, n-hexyl, and the like. As used in various tables herein, values of R' are represented as follows:

A = CH3, B = CH2CH2N(CH3)CH2—C6H6,

C = CH2CH2Br, D = CH2CH2F, E = CH2CF3, and

F = CH2CH2CH2Br.

The preferred compounds are those wherein R is loweralkyl, X is O, Ar is aryl, and R' is loweralkyl, halo-substituted loweralkyl, or (arylloweralkyl) (loweralkyl) aminoloweralkyl. More preferred compounds are those wherein R is methyl, X is O, Ar is aryl, and R' is halo-substituted loweralkyl or (arylloweralkyl) (loweralkyl) aminoloweralkyl. Still more preferred compounds are those wherein R is methyl, X is O, Ar is 3-halophenyl or 3-nitrophenyl, and R' is CH2CH2Br or CH2CH2N(CH3)CH2—C6H5. The most preferred compound is 2-(N-benzyl-N-methyl aminoethyl) 5-(3-chlorophenyl)-5,8-dihydro-1,3,7-trimethyl-2,4-dioxopyrido[2,3-d]pyrimidine-6-carboxylate.

The compounds of Formula I may generally be prepared via Hantzsch synthesis following the method of B. Loeu, et al., J. Med. Chem., 17, 956 (1974), by reacting an appropriately substituted 6-aminouracil of formula (II) with a stoichiometric equivalent of an intermediate of formula (III) according to the reaction:

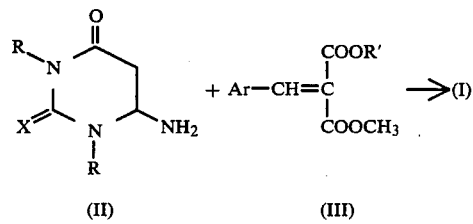

wherein R, Ar, R' and X are as defined above. This reaction should be conducted in a suitable organic acidic medium such as glacial acetic acid or propionic acid with heating (preferably at the reflux temperature of the solvent) and moisture should be excluded, for example by conducting the reaction under a blanket of dry nitrogen gas.

The intermediate of Formula (III) may be prepared by reacting a suitable aldehyde of Formula (IV) and an appropriately-substituted intermediate of formula (V) according to the reaction:

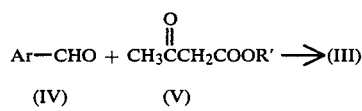

wherein Ar and R' are as defined above. This reaction may be conducted in a neutral organic solvent such as benzene, toluene, or the like with heating (preferably at the reflux temperature of the solvent) in the presence of a catalytic amount of an organic base such as pyridine or triethylamine. This intermediate of Formula (III) may be prepared and isolated prior to conducting its reaction with the uracil of Formula (II), or may conveniently be formed in situ.

In all of the foregoing descriptions and in the following preparations, the reaction products may be isolated from the reaction mixture and, if necessary of desired, further purified according to methodologies generally known in the art.

The intermediates of Formulas (II), (III), (IV), and (V) are generally known in the art or may be prepared according to art-known techniques. Such techniques are described, for example, in German published patent application 27,38,153 for intermediates (II), (IV), and (V) and in Knovenagel, Ber., 31, 143 (1898), for intermediate (III).

The compounds of Formula (I) have basic properties and therefore may be converted from the free bases to the therapeutically activity non-toxic, acid addition salts by treatment, with appropriate acids. Suitable inorganic acids are, for example, a hydrohalic acid, such as hydrochloric, hydrobromic, and the like; sulfuric acid, nitric acid, phosphoric acid, and the like. Appropriate organic acids include, for example, acetic, propanoic, hydroxyacetic, 2-hydroxypropanoic, 2-oxopropanoic, propanedioic, butanedioic, (Z)-2-butenedioic, (E)-2-butenedioic, 2-hydroxybutandioic, methanesulfonic, ethanesulfonic, benzenesulfonic, cyclohexanesulfanic, and the like organic acids. Conversely, the salt form may be converted by treatment with a suitable base (e.g., alkali such as sodium hydroxide) into the free base form.

The compounds of Formula I are useful for their calcium antagonist and anti-hypertensive activity as illustrated in the following tests.

Calcium antagonists are thought to act by blocking the inflow of calcium in the myocardium through discrete calcium channels in cell membranes. This antagonist activity suppresses that portion of myocardial or smooth muscle contractility which is dependent upon the influx of extracellular calcium.

The calcium channel antagonist activity of a compound may be demonstrated, for example, by its ability to inhibit depolarization-induced contraction of the vascular smooth muscle tissue from the rabbit aorta. This tissue can be made to contract when exposed to a depolarizing solution containing an elevated potassium ion concentration and normal amounts of calcium ions. A test compound added to the solution produces a dose-dependent relaxation of the contracted rabbit aortic tissue which gives an indication of calcium antagonist activity of the test compound. This test is described below as the "Rabbit Potassium Depolarized Blood Vessel Test".

Alternatively, one may evaluate the calcium antagonist activity of a test compound by measuring the displacement of nitrendipine to calcium channel antagonist receptors by the test compound according to the methods of Bolger, et al., Biochem. Biophys. Res. Comm., 104(4), 1604–1609 (1982) and Ehlert, et al., Life Sciences, 30, 2191–2202 (1982). In such a test, the amount of specifically-bound nitrendipine to rabbit heart is determined in the presence and absence of test compound. The percent nitrendipine displacement is directly related to the efficacy of the test compound as a calcium antagonist. This assay is described below as the "Nitrendipine Binding Assay". The antihypertensive activity of a test compound may be demonstrated by the "Spontaneously Hypertensive Rat Test" using a strain of rat such as that disclosed in Okamoto, et al., Jap. Circ. J., 270, 282 (1963). The general techniques for conducting such tests are disclosed in B. Vagnovsky "Automatic Blood-Pressure Measurements in Small Animals", American Laboratory, April, 1973, and "Techniques for the Measurement of Blood Pressure", Institute of Laboratory Animal Resouces NEWS, Vol. XIX (3), G 11–12, Spring, 1976. In this test a group of four male spontaneously hypertensive rats having systolic blood pressures greater than 150 mm Hg are used for each test compound. Systolic blood pressure is measured by the indirect method using a tail-cuff. The compounds are administered at a dose of 100 mg/kg body weight, and the average of the peak decrease in blood pressure is calculated for the four rats.

In the Rabbit Potassium Depolarized Blood Vessel Test, rabbits are killed by cervical dislocation, and the thoracic aorta is removed. Helical strips, approximately 30–40 mm in length, are cut from the aorta and are suspended in tissue baths of oxygenated Krebs bicarbonate buffer at 37° C. under a resting tension of 4 g. After an equilibration period of approximately 1–2 hours, the strips are challenged with a 30 mM potassium chloride solution and the peak contraction is measured. Following measurement of the peak contraction, the strips are washed and re-equilibrated for an hour in oxygenated Krebs bicarbonate buffer. After the re-equilibration of the aorta strips, the test compound was added to the bath at a concentration of $10^{-6}$M and the strips were allowed to stand for 10 minutes. After the 10 minute exposure to the test compound, the tissue strips were rechallenged with 30 mM potassium chloride solution and the maximum contraction was measured. The specificity of any inhibition of contraction is determined by addition of 10 mM phenylephrine.

The percent inhibition of contraction is calculated from the formula:

$$\% \text{ Inhibition} = 100 - (100 \times C_T/C_c)$$

where $C_T$ is the peak contraction in the presence of the test compound and $C_c$ is the peak contraction without test compound.

In the Nitrendipine Binding Assay, female New Zealand white rabbits are sacrificed by cervical dislocation, and the hearts are immediately removed, cleaned, chopped into small pieces, and homogenized in 5× volumes of 0.05M HEPES buffer, Ph 7.4. After the homogenate is centrifuged at 4,000 g for 10 min., the supernatent is recentrifuged at 42,000 g for 90 minutes. The resulting membrane pellet from the second centrifugation is resuspended in 0.05M HEPES buffer (Ph 7.4) and stored at −70° C. until used.

To conduct the binding assay, multiple tubes are prepared containing $^3$H-nitrendipine (0.05–0.50 nM), buffer, 0.10 ml of membrane, and test compound in a total volume of 1.0 ml. After this mixture has been allowed to react for 90 min. at 4° C., the bound nitrendipine is separated from the unbound nitrendipine by filtration of the mixture on Whatman GF/C filter. After the filters have been rinsed, they are dried and counted in a liquid scintillation counter. A tube without any test compound is used as the control. In order to determine the effect of test compounds on specific binding of nitrendipine, the non-specific binding of nitrendipine is determined both for each test compound and for the control by determining the amount of labeled nitrendipine bound to the rabbit membrane in the presence of excess unlabeled nitrendipine. The amount non-specifically bound material is subtracted from the total bound material to obtain the specifically-bound labeled nitrendipine. The results are reported as the concentration of test compound required to achieve 50% displacement of specifically-bound nitrendipine (IC 50).

Test results for exemplary compounds of Formula I are provided in Table I below, in which the Rabbit Potassium Depolarized Blood Vessel Test is called "Test 2", the Nitrendipine Binding Assay is called "Test 1" and the Spontaneously Hypertensive Rat test is called "Test 3". These results are given not for the purpose of limiting the invention thereto, but only to exemplify the useful pharmacological activities of all the compounds within the scope of Formula I.

TABLE I

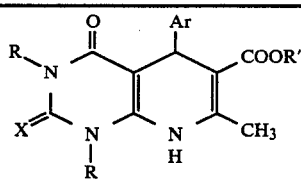

| Example | R | Ar | R' | X | Test 1 (IC50) | Test 2 (% Inhibition) | Test 3 (mmHg, 100 mpk) |
|---|---|---|---|---|---|---|---|
| I | $CH_3$ | 3-$NO_2$—Ph | A | O | $3 \times 10^{-7}$ | 54 | −11 |
| IV | $CH_3$ | 3-$NO_2$—Ph | B | O | $2.3 \times 10^{-7}$ | 44 | −28 |
| V | $CH_3$ | 3-CN—Ph | B | O | $6.5 \times 10^{-7}$ | 26 | −31 |
| II | $CH_3$ | 3-Cl—Ph | A | O | $1.0 \times 10^{-6}$ | 3 | −31 |
| VI | $CH_3$ | 3-Cl—Ph | B | O | $1.0 \times 10^{-7}$ | 52 | −50 |
| VII | H | 3-Cl—Ph | B | O | $8.0 \times 10^{-6}$ | | |
| VIII | $CH_3$ | 3-F—Ph | B | O | $5.0 \times 10^{-7}$ | 48 | −47 |
| IX | $CH_3$ | 3-$CH_3$O—Ph | B | O | $2.8 \times 10^{-6}$ | 8 | −57 |
| X | $CH_3$ | 3-$CH_3$—Ph | B | O | $3.2 \times 10^{-6}$ | 16 | −12 |
| XI | $CH_3$ | Ph | B | O | $1.3 \times 10^{-6}$ | 12 | −28 |
| XII | $CH_3$ | 2-$NO_2$—Ph | B | O | $2.5 \times 10^{-6}$ | 27 | −16 |
| XIII | $CH_3$ | 2-$NO_2$—Ph | B | O | | | −35 |
| XIV | $CH_3$ | 2-Cl—Ph | B | O | $1.0 \times 10^{-6}$ | 50 | −40 |
| XV | $CH_3$ | 2-furanyl | A | O | $1.0 \times 10^{-4}$ | | −22 |
| XVI | $CH_3$ | 2-furanyl | B | O | $2.0 \times 10^{-6}$ | | |
| III | $CH_3$ | 2-furanyl | B | O | $6.0 \times 10^{-6}$ | | −22 |
| XVII | $CH_3$ | cyclohexyl | B | O | $2.0 \times 10^{-6}$ | 18 | −30 |
| XVIII | $CH_3$ | 3-$CF_3$—Ph | B | O | $3.4 \times 10^{-6}$ | 33 | −37 |
| XIX | $CH_3$ | 3,5-di-Cl—Ph | B | O | $2.3 \times 10^{-6}$ | 28 | −37 |
| XX | H | 3-Cl—Ph | B | S | $> 10^{-6}$ | | −16 |
| XXI | $CH_3$ | 4-$CF_3$—Ph | B | O | $2.3 \times 10^{-6}$ | 6 | −16 |
| XXII | H | 3-$NO_2$—Ph | B | O | $7.7 \times 10^{-6}$ | | −11 |
| XXIII | $CH_3$ | 3-Cl—Ph | C | O | $7.8 \times 10^{-8}$ | 54 | −16 |
| XXIV | $CH_3$ | 3-$NO_2$—Ph | C | O | $1.09 \times 10^{-7}$ | 26 | −10 |
| XXV | $CH_3$ | 3-$CF_3$—Ph | C | O | $1.1 \times 10^{-6}$ | 41 | |
| XXVI | $CH_3$ | 3-Cl—Ph | D | O | $8.9 \times 10^{-7}$ | | |
| XXVII | $CH_3$ | 3-Cl—Ph | E | O | $8.6 \times 10^{-7}$ | | |
| XXVIII | $CH_3$ | 2-Cl—Ph | C | O | $1.75 \times 10^{-7}$ | 23 | |
| XXIX | $CH_3$ | 3-Cl—Ph | F | O | $3.85 \times 10^{-7}$ | 44 | |

In view of their calcium antagonist and anti-hypertensive properties, the compounds of Formula I and their acid addition salts are useful in the treatment of diseases and conditions caused by or resulting in excessive calcium channel activity or hypertension. Such conditions are described in "Calcium Blockers:Mechanisms of Action and Clinical Applications", S. F. Flaim and R. Zelis, eds., Urban & Schwarzenberg, Inc., Baltimore, MD, 1982, and include angina, pulmonary hypertension, arrhythmia, cerebral ischemia, and myocardial infarction.

To prepare the pharmaceutical compositions of this invention, an effective antihypertensive or calcium channel inhibiting amount of the particular compound, in free base or acid addition salt form, is combined as the active ingredient in intimate admixture with a pharmaceutically acceptable carrier, which carrier may take a wide variety of forms depending on the form of preparation desired for administration.

These pharmaceutical compositions are desirably in unitary dosage form, preferably suitable for administration orally, rectally, or by parenteral injection. For example, in preparing the compositions in oral dosage form, any of the usual pharmaceutical media may be employed, such as for example water, glycols, oils, alcohols, and the like in the case of oral liquid preparations, such as suspension, syrups, elixirs, and solutions; or solid carriers, such as starches, sugar, kaolin, lubricants, binders, disintegrating agents, and the like in the case of powders, pills, capsules, tablets, or the like oral solid preparations. Because of their ease in administration, tablets and capsules represent the most advantageous oral dosage unit form, in which case solid pharmaceutical carriers are obviously employed. For parenteral compositions, the carrier will usually comprise sterile water, at least in large part, although other ingredients (e.g., to aid solubility) may be included. Injectable solutions may be prepared, for example, in which the carrier comprises saline solution, glucose solution, or a mixture of saline and glucose solution. Injectable suspensions may also be prepared in which case appropriate liquid carriers, suspending agents, and the like may be employed.

Acid addition salts of (I) are obviously more suitable in the preparation of aqueous compositions due to their increased water solubility over the corresponding free base form.

It is especially advantageous to formulate the aforementioned pharmaceutical compositions in dosage unit form for ease of administration and uniformity of dosage. The term "dosage unit form" as used in the specification and claims herein, refers to physcially discrete units suitable as unitary dosages, each unit containing a pre-determined quantity of active ingredient calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls, and the like, and segregated multiples thereof. Oral dosage unit forms containing from about 10 to about 250 mg of a compound of the invention are preferred.

The present invention also provides a method of treating hypertension in a warm-blooded animal (including man) suffering from hypertension by administering to the animal in need of same an effective antihypertensive amount of a compound of formula (I) or a pharmaceutically acceptable acid addition salt thereof.

The present invention further provides a method inhibiting of calcium channel activity in a warm-blooded animal (including man) in need of such inhibition by administering to the animal in need of same an effective calcium channel inhibiting amount of a compound of formula (I) or a pharmaceutically acceptable acid addition salt thereof.

The following examples are intended to illustrate and not to limit the scope of the present invention. Unless otherwise noted herein all parts are by weight.

EXAMPLE I

Methyl 5,8-Dihydro-1,3,7-trimethyl-5-(3-nitrophenyl)-2,4-dioxopyrido[2,3-d]pyrimidine-6-carboxylate A mixture of 6-amino-N,N'-dimethyluracil (3.1 g,20 mM),3-nitrobenzaldehyde (3 g,20 mM), and methyl acetoacetate (2.3 g, 1.4 ml, 20 mM) in glacial acetic acid (10 ml) was stirred under $N_2$ at reflux for 3 hours, cooled to ambient, light yellow solid which was filtered and rinsed with acetone to give the title compound (1.04 g,13.5%),mp >230° C.

EXAMPLE II

Methyl 5-(3-Chlorophenyl)-5,8-dihydro-1,3,7-trimethyl-2,4-dioxopyrido[2,3-d]pyrimidine-6-carboxylate A mixture of 6-amino-N,N'-dimethyluracil (1.5 g, 10 mM) and methyl 2-(3-chlorobenzylidene)acetoacetate (2.38 g, 10 mM) in glacial acetic acid (20 ml) was stirred at reflux under $N_2$ for 3 hrs., cooled to ambient, evaporated in vacuo and diluted with acetone to precipitate out the product. Recrystallization from MeOH/Acetone gave the title compound (2.0 g,53%), mp. 230° C.

EXAMPLE III 2-(N-Benzyl-N-methylamino)ethyl 5-(Furan-2-yl)-5,8-dihydro-1,3,7-trimethyl-2,4-dioxopyrido[2,3-d]pyrimidine-6-carboxylate Monohydrochloride Monohydrate A stirring solution of 2-(N-benzyl-N-methylamino)ethyl-5-(furan-2-yl)-5,8-dihydro-1,3,7-trimethyl-2,4-dioxopyrido [2,3-d]pyrimidine-6-carboxylate (2.0 g, 0.004 M; Example XVI) in methanol (100 ml) was adjusted to pH≈1 via dropwise addition of concentrated HCl. Evaporation of solvent gave a brown oil, which was dissolved in methanol and treated with activated charcoal. Filtration of the solution to remove the charcoal and evaporation of solvent from the filtrate gave a yellow solid residue which was crystallized with acetone to give 1.42 g (75%) of the title compound as a pale yellow crystalline salt mp. 135°-138° C.

EXAMPLES IV - XXIX

Following the procedure of Example II but substituting the equivalent amounts of the appropriate starting materials, these are prepared the following compounds. The hydrochloride salts are formed by treating the corresponding free bases with concentrated hydrochloric acid in methanol following the procedure of Example III.

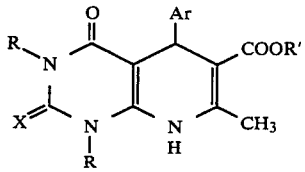

| Example | R | Ar | R | X | Salt | m.p. (°C.) |
|---|---|---|---|---|---|---|
| IV | CH₃ | 3-NO₂—Ph | B | O | HCl | 231–234 |
| V | CH₃ | 3-CN₂—Ph | B | O | HCl | 207–210 |
| VI | CH₃ | 3-Cl—Ph | B | O | HCl | 45 (free base) |
| VII | H | 3-Cl—Ph | B | O | HCl | 235–230 |
| VIII | CH₃ | 3-F—Ph | B | O | HCl | 230–234 (free base) |
| IX | CH₃ | 3-CH₃O—Ph | B | O | HCl | 201–204 |
| X | CH₃ | 3-CH₃—Ph | B | O | HCl | 208–212 |
| XI | CH₃ | Ph | B | O | HCl | 210–213 |
| XII | CH₃ | 2-NO₂—Ph | B | O | HCl | 261–264 |
| XIII | CH₃ | 2-NO₂—Ph | B | O | — | 192–194 |
| XIV | CH₃ | 2-Cl—Ph | B | O | HCl | 226–230 |
| XV | CH₃ | 2-furanyl | A | O | HCl | 225–227 |
| XVI | CH₃ | 2-furanyl | B | O | HCl | 135–138 |
| XVII | CH₃ | cyclohexyl | B | O | HCl | 202–205 |
| XVIII | CH₃ | 3-CF₃—Ph | B | O | HCl | 158–161 |
| XIX | CH₃ | 3,5-di-Cl—Ph | B | O | HCl | 247–250 |
| XX | H | 3-Cl—Ph | B | S | HCl | 228–231 |
| XXI | CH₃ | 4-CF₃—Ph | B | O | HCl | 225–228 |
| XXII | H | 3-NO₂—Ph | B | O | HCl | 245–248 |
| XXIII | CH₃ | 3-Cl—Ph | C | O | — | 195–198 |
| XXIV | CH₃ | 3-NO₂—Ph | C | O | — | 188–191 |
| XXV | CH₃ | 3-CF₃—Ph | C | O | — | 216–220 |
| XXVI | CH₃ | 3-Cl—Ph | D | O | — | 268–272 |
| XXVII | CH₃ | 3-Cl—Ph | E | O | — | 242–245 |
| XXVIII | CH₃ | 2-Cl—Ph | C | O | — | 263–267 |
| XXIX | CH₃ | 3-Cl—Ph | F | O | — | 190–194 |

The preceding Examples have been provided only for illustration of the subject invention and not to limit its scope, which is described only in the appended claims.

What is claimed is:

1. A compound having the formula

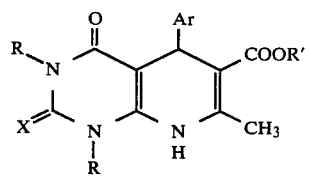

and the pharmaceutically acceptable acid addition salts thereof, wherein:

R is hydrogen or loweralkyl;

Ar is aryl, furanyl, or cyclohexyl;

R' is loweralkyl, loweralkyl substituted with one halo or trifluoromethyl group, or (arylloweralkyl)-(loweralkyl)aminoloweralkyl; and X is O or S;

said aryl being phenyl or phenyl substituted with one or two substituents independently selected from halo, nitro, cyano, loweralkyl, loweralkyloxy, and trifluoromethyl.

2. The compound of claim 1 wherein

R is lowerlkyl,

X is O,

Ar is aryl, and

R' is loweralkyl, halo-substituted loweralkyl, or (arylloweralkyl) (loweralkyl) aminoloweralkyl.

3. The compound of claim 1 wherein

R is methyl,

X is O,

Ar is aryl, and

R' is halo-substituted loweralkyl or (arylloweralkyl)(loweralkyl) aminoloweralkyl.

4. The compound of claim 1 wherein R is methyl, X is O, Ar is 3-halophenyl or 3-nitrophenyl, and R' is $CH_2CH_2Br$ or $CH_2CH_2N(CH_3)CH_2-C_6H_5$.

5. The compound of claim 1 wherein R is methyl, X is O, Ar is 3-chlorophenyl, and R' is $CH_2CH_2Br$ or $CH_2CH_2N(CH_3)CH_2-C_6H_5$.

6. The compound of claim 1 which is 2-(N-benzyl-N-methylamino)ethyl 5-(3-chlorophenyl)-5,8-dihydro-1,3,7-trimethyl-2,4 dioxopyrido[2,3-d]pyrimidine-6-carboxylate.

7. A pharmaceutical composition comprising an effective anti-hypertensive amount of a compound of claim 1 in admixture with a pharmaceutically acceptable carrier.

8. A pharmaceutical composition comprising an effective calcium channel inhibiting amount of a compound of claim 1 in admixture with a pharmaceutically acceptable carrier.

* * * * *